United States Patent [19]

Bottorff

[11] Patent Number: 5,252,754
[45] Date of Patent: Oct. 12, 1993

[54] FLUORINATED ALDOKETENE DIMER STRUCTURES AND THEIR USE AS COMBINATION OIL AND WATER RESISTANT SIZES FOR CELLULOSIC MATERIALS

[75] Inventor: Kyle J. Bottorff, Newark, Del.

[73] Assignee: Hercules Incorporated, Wilmington, Del.

[21] Appl. No.: 794,087

[22] Filed: Nov. 18, 1991

[51] Int. Cl.$^5$ ............................................. C07D 305/12
[52] U.S. Cl. ..................................... 549/328; 549/329; 549/510; 549/511; 162/158; 162/168.7; 162/164.7
[58] Field of Search ................. 549/510, 511, 328, 329

[56] References Cited

U.S. PATENT DOCUMENTS

| | | | |
|---|---|---|---|
| 3,280,150 | 10/1966 | England et al. | 260/343.5 |
| 3,362,965 | 1/1968 | England et al. | 260/343.9 |
| 3,795,684 | 3/1974 | Domba | 260/343.9 |
| 4,419,298 | 12/1983 | Falk et al. | 260/501.17 |
| 4,426,466 | 1/1984 | Schwartz | 523/455 |
| 4,590,236 | 5/1986 | König et al. | 524/460 |

OTHER PUBLICATIONS

Kirk-Othmer Encyclopedia of Chemical Technology, Third edition, vol. 16, pp. 808-814, 1981; Pub. John Wiley & Sons.

*Primary Examiner*—C. Warren Ivy
*Assistant Examiner*—Ba K. Trinh
*Attorney, Agent, or Firm*—Roy V. Jackson

[57] ABSTRACT

Aldoketene dimer sizing agents that can efficiently impart both oil and water sizing properties to paper, of an unsaturated $\beta$-lactone structure containing terminal perfluoralkyl groups separated from the ketene moiety by at least three carbon atoms, which may be attached to a halogen other than fluorine or an ether, thioether, amide, tertiary amine, ester, or side chain functionality.

2 Claims, No Drawings

FLUORINATED ALDOKETENE DIMER STRUCTURES AND THEIR USE AS COMBINATION OIL AND WATER RESISTANT SIZES FOR CELLULOSIC MATERIALS

This invention relates to sizing agents for paper, and particularly to sizing agents that impart both oil and water sizing properties to paper.

BACKGROUND OF THE INVENTION

There is a long felt need for a single chemical that can efficiently impart both oil and water sizing properties to paper, since many grades of paper require both oil resistance and water resistance. Commercially available chemicals that are said to provide both oil and water sizing properties are not in fact efficient water sizing agents. Consequently, when both oil and water sizing properties are required, the conventional practice is to use an oil sizing agent and a separate water sizing agent. The effect is to reduce the efficiency of both the oil sizing agent and the water sizing agent.

Many end uses of paper products require that these cellulosic materials be resistant to penetration by various liquids ranging from water to hot oil and grease. Although many known chemicals act as efficient oil or water sizing agents for paper, few of them act as both water and oil sizing agents, and none of those provide efficient sizing against penetration by water, hot water, oil, and hot-oil. Reference is made in this connection to Kirk Othmer Encyclopedia of Chem. Tech., 3d ed, v 16, p. 808-814, 1981; "The Sizing of Paper", 2nd Ed., W. F. Reynolds Editor, Tappi Press, 1989.

Examples of end use products requiring some combination of water, hot water, oil or hot oil resistance include textile products, leather goods, reprographic paper, food board containers, wax coated paper, labels, coupons, food wrap, pet food containers, nonwoven medical wear, candy wraps, food containers for use in microwave ovens, and molded food containers.

Commercial papermaking conditions require that any chemical additive, such as a sizing agent, must be either readily water dispersible in its neat form, or easily convertible into a water dispersible emulsion or stable aqueous dispersion.

There are two physical forms of sizing agents in aqueous delivery systems: monomolecularly dispersed ionic salts and dispersions or emulsions of particulates or oils. Sizing agents in particulate form must be low-melting solids or liquids so the material will spread throughout the paper when heated in the dryer section of a paper machine.

When the sizing agent is added to the pulp slurry (internal addition) it must adhere to the pulp or it will not be retained in the paper. This may be accomplished by means of opposite charge attractions between the pulp and the size and by physical trapping of particles of size during web formation.

For efficient oil and water sizing, both hydrophobic and oleophobic constituents of the size molecules must be oriented away from the paper and hydrophilic constituents oriented towards the paper, so that liquid penetrants are exposed to a low surface energy hydrophobic and oleophobic surface. The sizing agent must maintain that molecular orientation to function efficiently. This orientation can be maintained by opposite charge bonding, ionic bonding, or by covalent bonding between the size and the pulp. Covalent bonding is the strongest form of bonding. Weaker opposite charge and ionic bonds are more susceptible to cleavage by aqueous liquid penetrants, especially when the penetrants are hot.

Efficient commercial oil sizing agents for paper also contain hydrophilic functional groups, such as phosphate, carboxylate, or chromium salts, that maintain water dispersiblity, which is needed to enable the size to be applied to the paper in an aqueous vehicle, the most practical way. Of course, hard water causes these salts to precipitate out of solution, which lowers their sizing efficiency and causes deposit problems on paper machines.

The most efficient oil-sizing agents for cellulosic materials contain long, linear fluorocarbon chains. Fluorocarbons, in general, have very low surface energies and are not wet easily by oil based materials, but salts that contain fluorocarbon hydrophobes are inefficient water sizing agents. Some agents that contain fluorocarbon hydrophobes but no hydrophilic salt groups do provide both water and oil sizing, but their level of water sizing is very low. Conversely, chemicals that contain hydrocarbon hydrophobes are efficient water sizing agents, but are inefficient oil sizing agents. Consequently, in a combination of a fluorocarbon based product for oil resistance and a hydrocarbon-based product for water resistance, each product has an adverse effect on the other's performance.

For instance, the inclusion of a hydrocarbon based size such as an alkyl ketene dimer (AKD) decreases the ability of a fluorochemical size to resist oil and grease penetration and requires more fluorochemical to attain the required level of oil resistance.

Ketene dimers, which are β-lactones of 3-hydroxy 3-butenoic acids, have the generic structure

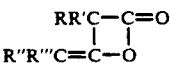

When R' and R''' are hydrogen, the compounds are referred to as aldoketene dimers.

The aldoketene dimer in which R, R', R'', and R''' are H is the one commonly referred to as ketene dimer. Aldoketene dimers are typically produced by letting the precursor aldoketenes spontaneously dimerize, as follows:

The preparation of the aldoketenes is well known, for instance from S. Patai, "The Chemistry or Ketenes, Allenes, and Related Compounds", J. Wiley and Sons 1980., which discloses that when R is a perfluoroalkyl group (R$_f$), no aldoketene dimers are formed:

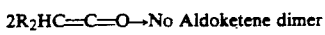

In the alkyl ketene dimer (AKD) that is sold commercially as a sizing agent for cellulosic materials, R and R'' are long chain alkyl groups. Other variations of R and R'' include R groups that contain alkyl, ester, ketone, ether, isocyanate, aryl, chloro, bromo, and heptafluoroisopropoxy functionalities.

U.S. Pat. No. 3,795,684 discloses a heptafluoroisopropoxy group on a β-lactone, but fails to suggest that its sizing ability extends beyond "water repellency"

which follows from the fact that the fluorinated segment of the molecule is very short and branched.

U.S. Pat. No. 3,362,965 discloses "mixed" aldoketene-ketoketene β-lactones produced by the reaction of aldoketenes, RHC=C=O, with perfluorinated ketoketenes, $(R_f)_2C=C=O$, without any suggestion of sizing ability other than water repellency.

There is a clear need for an efficient size such as an alkyl ketene dimer that has the ability of a fluorochemical size to resist oil and grease penetration without the inhibiting effect of a separately added fluorochemical.

SUMMARY OF THE INVENTION

An aldoketene dimer having the structure:

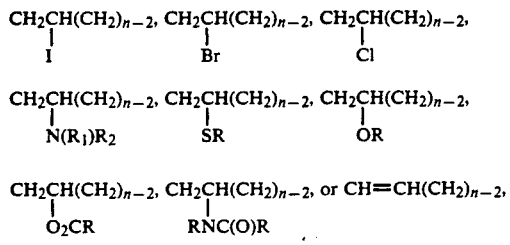

in which y=1-18, Z=$(CH_2)_n$, $$CH_2CH(CH_2)_{n-2}, \quad CH_2CH(CH_2)_{n-2}, \quad CH_2CH(CH_2)_{n-2},$$
$$\quad | \qquad\qquad\qquad | \qquad\qquad\qquad |$$
$$\quad I \qquad\qquad\qquad Br \qquad\qquad\qquad Cl$$

$$CH_2CH(CH_2)_{n-2}, \quad CH_2CH(CH_2)_{n-2}, \quad CH_2CH(CH_2)_{n-2},$$
$$\quad | \qquad\qquad\qquad\quad | \qquad\qquad\qquad |$$
$$N(R_1)R_2 \qquad\qquad SR \qquad\qquad\qquad OR$$

$$CH_2CH(CH_2)_{n-2}, \quad CH_2CH(CH_2)_{n-2}, \text{ or } CH=CH(CH_2)_{n-2},$$
$$\quad | \qquad\qquad\qquad\quad |$$
$$O_2CR \qquad\qquad\quad RNC(O)R$$

in which R, $R_1$ and $R_2$ are each any alkyl radical, and n is an integer from 3 to 18 inclusive.

Perfluorinated precursor aldoketenes of the said dimers can be prepared from carboxylic acid chlorides that contain perfluoroalkyl groups (linear or branched) effectively spaced from the acid chloride moiety by the terminal perfluorinated spacing groups represented by "Z" in the structure,

$R_fZCCl$.

Surprisingly, when the perfluoroalkyl groups are spaced from the ketene moiety, >C=C=O, the impossibility of spontaneous dimerization that characterizes the perfluoroalkyl aldoketones disclosed in the above Patai reference is no longer encountered.

The perfluorinated ketene dimers are formed according to the invention by mixing a fluorinated carboxylic acid chloride having the structure:

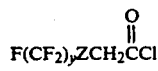
$F(CF_2)_yZCH_2CCl$ in which y=1-18 and $$Z = (CH_2)_n, \quad CH_2CH(CH_2)_{n-2},$$
$$\qquad\qquad\qquad\quad |$$
$$\qquad\qquad\qquad\quad I$$

$$CH_2CH(CH_2)_{n-2}, \quad CH_2CH(CH_2)_{n-2}$$
$$\quad | \qquad\qquad\qquad\quad |$$
$$\quad Br \qquad\qquad\qquad\quad Cl$$

or $CH=CH(CH_2)_{n-2}$ with n=an integer from 3-18, with a trialkyl amine, preferably in a slight molar excess of the amine and in an aprotic organic solvent.

The carboxylic acid chlorides, which are known from, for instance, U.S. Pat. Nos. 3,016,406 and 3,145,222, may be made by the treatment with thionyl chloride, oxalyl chloride, phosphorous pentachloride, or phosphorous trichloride, of a fluorinated carboxylic acid having the structure:

$F(CF_2)_yZCO_2H$ in which y, Z, and n are as described previously.

The perfluorinated ketene dimers of the invention exhibit unusually high levels of both water and oil repellency when applied to paper and shaped articles made from cellulosic materials. An advantage of these compounds is that they can be emulsified in water to make sizing treatment compositions according to the invention, that impart an efficient combination of oil, hot oil, water and hot water sizing that impart water, hot-water, oil, and hot-oil repellency, and comprise:

(a) fluoroaliphatic radical-containing aldoketene dimers of β-lactone structure as described above, and
(b) cationic starch, an emulsifier, and water.

The sizing compositions may also contain water soluble cationic polyamine or polyamide epoxide resins to enhance emulsion stability, chemical retention, and performance. They can be added internally as the paper is being formed in a conventional manner or applied to preformed paper. Surface application of the aldoketene dimers to paper may also be made from organic solvent solutions.

This new class of sizing composition can be referred to as fluorinated alkyl ketene dimer dispersions/emulsions and represented for convenience by the abbreviation $R_fAKD$. The invention particularly contemplates their use to impart water, hot-water, oil, and hot oil resistance to biodegradable cellulose molded articles, thus providing an alternative to non-biodegradable polystyrene.

DETAILED DESCRIPTION OF THE INVENTION

The preparation of the aldoketene dimers according to the invention, by mixing a fluorinated carboxylic acid chloride of the structure:

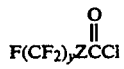
$F(CF_2)_yZCCl$ in which y=1-18, and Z=$(CH_2)_n$, $CH_2CH(X)(CH_2)_{n-2}$, or $CH=CH(CH_2)_{n-2}$ with n=an integer from 3-18 and X=I, Br, or Cl with a trialkyl amine, is preferably run in the presence of an any aprotic, organic solvent in which the reagents are soluble, more preferably in ether, methylene chloride, or dichloropropane. Preferably y=4-14, and also preferably a slight molar excess of triethyl amine is present (1.02 to 1.25 molar equivalents, more preferably 1.04 to 1.12 and most preferably 1.08 molar equivalents).

The acid chloride is preferably added to the amine at a controlled rate such that the temperature of the reaction medium remains between zero and 90° C., more preferably between 20° and 50° C. and most preferably between 40° and 45° C. The desired temperature is conventionally determined according to such known factors as reagent solubility and product stability. The use of a trialkyl amine other than the preferred triethyl amine is limited by conventional considerations to avoid alkyl groups that are too bulky to hinder the progress of the reaction.

The standard procedure included sparging the solvent with an inert gas and maintaining an inert gas atmosphere, however, this is not a necessity of the invention.

The dimer product can be dissolved in ether and extracted with water and brine to remove traces of triethylammonium hydrochloride from the product. The ether solution would then be dried and concentrated under reduced pressure to provide the dimer in a more pure state; however, this is not a necessity of the invention.

Although the aldoketene dimers of the invention are capable of dimerization to $\beta$-lactone structures, unlike fluorinated aldoketenes of the structure $R_fCH=C=O$, the conventional considerations that apply to the preparation of ketenes make it desirable to exclude moisture and other known nucleophiles such as alcohols, thiols, primary amines, and secondary amines from the reaction mixture to hinder the formation of undesired side products such as carboxylic acids, carboxylic acid anhydrides, esters, thioesters, and amides.

The fluorinated carboxylic acids can be conventionally prepared by combining a perfluorinated alkyl halide having the structure:

$$F(CF_2)_y X$$

where $y=1-18$ and $X=I$, Br, or Cl, with an terminally unsaturated carboxylic acid having the structure:

$$CH_2=CH(CH_2)_p CO_2 H$$

where $p=0-15$, in the presence of any free radical catalyst. Some transition metal catalysts can be used in place of the free radical catalysts, as disclosed, for instance, by C. Qing-yun and Y. Nong-yu, Acta Chim. Sinica 1118, 1985, C. Qing yun and Z-Y. Yang J. Fluor. Chem., 28, 399, 1985, K. Von Werner, J. Fluor. Chem., 28, 229, 1985, Qing yun and Z-Y. Yang, J. Fluor. Chem., 36, 149, 1987, and T. Ishihara and M. Kuroboshi, Synth. Comm. 19, 9 and 10, 1611, 1989. These include palladium (0), copper, ruthenium, platinum, silver, nickel, tungsten, chromium, manganese, rhodium, and molybdenum, magnesium, lead and tin.

Fluorinated carboxylic acids can also be conventionally prepared from perfluoroalkylsulfonyl chlorides. Many perfluoroalkyl halides and terminally unsaturated carboxylic acids are sold commercially.

The unsaturated $\beta$-lactone moiety of the fluorinated aldoketene dimer structures can be identified by the following analysis techniques:

(1) Infrared spectroscopy (IR): characteristic unsaturated $\beta$-lactone carbonyl vibrations between 1865–1875 and 1830–1845 cm$^-$, combined with characteristic unsaturated $\beta$-lactone olefin vibrations between 1715 and 1730 cm$^{-1}$.

(2) Carbon 13 nuclear magnetic resonance spectroscopy (C$^{13}$ NMR): characteristic proton decoupled peaks at 167–171, 143–149, 98–104, and 53–59 ppm.

(3) Hydrogen 1 nuclear magnetic resonance spectroscopy (H$^1$NMR): characteristic olefin proton resonance at 4.5–5.0 ppm and resonance for proton $\alpha$ to carbonyl at 3.8–4.0 ppm.

The perfluorinated alkyl moiety $[F(CF_2)n—]$ can be identified by:

(1) Infrared spectroscopy (IR): characteristic very strong absorptions between 1180 and 1250 cm$^{-1}$.

(2) C$^{13}$ NMR characteristic carbon fluorine splitting patterns between 105 and 130 ppm.

The aqueous $R_f$AKD dispersions/emulsions are very stable. Outstanding oil, grease and water resistant paper can be achieved by convenient, direct addition of the $R_f$AKD dispersions/emulsions to the pulp slurry as the paper is being made or by surface application after the paper is formed. The $R_f$AKD can also be surface applied to preformed paper from an organic solvent solution. They are not precipitated by cations from hard water, unlike the anionic salts contained in commercial oil-sizing agents, and the use of water softening agents is avoided.

The $R_f$AKD sizing agents of the invention form covalent bonds to cellulose fibers under conditions existing on commercial paper machines using the heat from the paper machine, and thus avoid disruption of the bonding by acidic, basic, or neutral aqueous penetrants.

Emulsions/dispersions are preferably prepared by homogenization of an aqueous mixture of cooked starch, sodium lignin sulfonate (SLS), melted $R_f$AKD, or $R_f$AKD dissolved in a non water miscible solvent, and sodium naphthalene sulfonate (SNS). A bacteriostat can be added as a preservative if needed. The ratios by weight on a dry basis are 0.5–6.0 parts cationic starch, preferably 0.7–3.0 parts starch, and most preferably 1.09 parts starch, 0.05–0.50 parts SLS, preferably 0.07–0.030 parts SLS, and most preferably 0.19 SLS, 0.05–0.50 parts of SNS, preferably 0.10–0.30, and most preferably 0.17 parts of sodium naphthalene sulfonate, 0.01–25 parts of $R_f$AKD, preferably 3–20 parts of $R_f$AKD, and most preferably 4.5–12 parts of $R_f$AKD, and 65–99 parts of water, preferably 80–96 parts water and most preferably 85–94 parts of water.

The most preferred starch is a low molecular weight (7 centipoise viscosity at 5% starch in water), tertiary amine derivative (0.27% N) starch. A wide variety of starches can be used. These include starches of varying molecular weight and varying degree of tertiary amine or quaternary amine derivation. Surfactants other than SLS and sodium naphthalene sulfonate can also be used.

It is preferred that the $R_f$AKD materials be in a liquid state during homogenization to make a stable, efficient sizing emulsion/dispersion. This can be accomplished by adding the $R_f$AKD as a non aqueous miscible solvent solution or by homogenizing the mixture at a temperature above the melting point of the $R_f$AKD. The organic solvents can be removed from the emulsion/dispersion under reduced pressure.

The homogenization can be accomplished at 3000–9500 psi, more preferably at 5000–8500 psi, and most preferably at 7000–7500 psi.

The $R_f$AKD emulsion/dispersions are characterized by their milky off white to white appearance. Preferably their average emulsion droplet/dispersion particle size is 0.10–1.50 microns, more preferably 0.20–0.80 microns, and most preferably 0.25–0.35 microns. Such emulsion/dispersions are sufficiently stable to avoid agglomeration over a period of months at ambient temperatures. Emulsion/dispersions having an average particle size greater than 0.70 are stable for short periods, but begin phase separation after standing for 30 minutes.

The usefulness of the $R_f$AKD emulsion/dispersions is easily demonstrated by applying the emulsion/dispersions to paper internally or on the surface at low dosage levels and noting the degree of water and oil sizing (see examples).

DEFINITIONS:

mp—Melting Point
ms—Mass Spectroscopy
$C^{13}$ NMR—Carbon 13 Nuclear Magnetic Resonance Spectroscopy
$H^1$ NMR—Hydrogen 1 Nuclear Magnetic Resonance Spectroscopy
s—Singlet
d—Doublet Peaks
t—Triplet Peaks
br m—Broad multiplet Peaks
IR—Infrared Spectroscopy
S—Strong Peak
VS—Very Strong Peak
$R_f$—Perfluorinated linear carbon chain
THF—Tetrahydrofuran
BW—Basis Weight
AKD—Alkyl Ketene Dimer
DCP—1,2-Dichloropropane
ppm—parts per million Sizing promoter resin a resin that increases the rate at which the ultimate size cure is obtained in sized paper, for example, Resin 2399, sold by Hercules Incorporated, which is a cationic resin made by reacting diethylenetriamine, dicyandiamide, and epichlorohydrin.

The following examples illustrate specific embodiments of the invention.

EXAMPLE 1

General Procedure for Preparation of Fluorinated $\beta$-Lactone Aldoketene Dimers: A dry reaction vessel fitted with a water reflux condenser, overhead stir, constant pressure addition funnel, and thermometer was charged with 2-3 parts of 1,2-dichloropropane by weight. The solution was sparged with argon for 10 minutes and further charged with 1.08-1.15 molar equivalents of triethyl amine while maintaining an argon atmosphere. One molar equivalent of fluorinated carboxylic acid chloride, neat or diluted with 1,2 dichloropropane, was introduced to the stirred mixture in a dropwise fashion at such a rate to keep the reaction mixture below 45° C. The acid chloride may need to be heated prior to addition to assure a totally liquid form of the acid chloride was being added to the reaction mixture. After addition of the acid chloride was complete, the reaction mixture was heated and held at 40°-45° C. for 60-90 minutes. The reaction was filtered and the filter cake (triethylammonium hydrochloride) was rinsed with anhydrous ether or 1,2 dichloropropane (DCP). The ether and DCP were warmed to 25°-75° C. prior to rinsing. The combined filtrates are concentrated under reduced pressure to provide fluorinated $\beta$-lactone aldoketene dimer. The dimer product is dissolved in ether and extracted with water and brine to remove traces of triethylammonium hydrochloride from the product, and the ether solution dried and concentrated under reduced pressure to provide the dimer in a more pure state.

General characteristic spectral data which demonstrates the unique molecular structure combination of an aldoketene dimer (unsaturated $\beta$-lactone) and perfluorinated hydrocarbon tails follow: $H^1$ NMR (CDCl$_3$) olefin proton comes at 4.6-4.8 (t, 1 H), proton on $\beta$-lactone comes at 3.9-4.0 (t, 1 H), allylic protons and protons $\alpha$ to perfluoroalkyl groups come at 2.0-2.14 (m, 6 H) ppm; IR (Neat) $\beta$-lactone carbonyl at 1865-75 (VS), exocyclic $\beta$-lactone olefin at 1725-30 (VS), perfluoroalkyl at 1200 (br, VVS) cm$^{-1}$; C$^{13}$ NMR (CDCl$_3$) (proton decoupled) carbon $\alpha$ to perfluoroalkyl group comes at 30-32 ppm as a triplet, exocyclic olefin carbon comes at 100-103 ppm, endocyclic olefin carbon comes at 144-147 ppm, $\beta$-lactone carbonyl comes at 168-171 ppm, perfluorinated carbons come between 112-122 ppm as multiplets, carbon-$\alpha$ to carbonyl on $\beta$-lactone comes at 52-55 ppm. This data is representative of all the R$_f$AKD compounds synthesized.

EXAMPLE 2

Preparation of Fluorinated $\beta$-Lactone Aldoketene Dimer With y=4, and Z=(CH$_2$)$_9$: a dry reaction vessel fitted with a water reflux condenser, overhead stir, constant pressure addition funnel, and thermometer was charged with 200 g of 1,2-dichloropropane. The solution was sparged with argon for 10 minutes and further charged with 26.5 g (262.3 mmol) of triethyl amine while maintaining an argon atmosphere. 11-perfluorobutylundecanoyl chloride (95.55 g, 226.15 mmol) was introduced to the stirred mixture in a dropwise fashion over a period of 75 minutes. The reaction mixture was heated and held at 40°-45° C. for 90 minutes. The reaction was filtered and the filter cake (triethylammonium hydrochloride) was rinsed with anhydrous ether. The combined filtrates were concentrated under reduced pressure to provide 83.1 g (88%) of dimer. Characteristic physical data: mp 25°-28° C.; characteristic spectral data: see general procedure.

EXAMPLE 3

Preparation of Fluorinated $\beta$-Lactone Aldoketene Dimer With y =4 (<4%),6 (35%), 8 (30%), 10 (17%), 12 (8%),14 or more (<6%) and Z=CH$_2$)$_9$: Following the general procedure, 55.5 g (89.2 mmol) of 11-perfluoroalkylundecanoyl chloride (CF$_2$ perfluoro homolog distribution as shown above) was added to a mixture of 180.3 g of 1,2-dichloropropane and 10.02 g (99 mmol) triethyl amine. After work up, 49.9 g of aldoketene dimer was obtained. Characteristic data: mp 45°-48° C. Characteristic spectral data: see general procedure.

EXAMPLE 4

Preparation of Fluorinated $\beta$-Lactone Aldoketene Dimer With y =4 (<4%),6 (35%), 8 (30%), 10 (17%), 12 (8%),14 or more (<6%) and Z=(CH$_2$)$_5$: Following the general procedure, 15.0 g (26.5 mmol) of 7 perfluoroalkylheptanoyl chloride (CF$_2$ perfluoro homolog distribution as shown above) was added to a mixture of 50 g of 1,2-dichloropropane and 2.83 g (28.1 mmol) triethyl amine. After work up, 11.6 g of aldoketene dimer was obtained. Characteristic data: mp 60°-62° C. Characteristic spectral data: see general procedure.

EXAMPLE 5

Preparation of Fluorinated $\beta$-Lactone Aldoketene Dimer With y =4 (<4%),6 (35%), 8 (30%), 10 (17%), 12 (8%),14 or more (<6%) and Z=CH$_2$)$_3$: Following the general procedure, 10.0 g (18.7 mmol) of 5-perfluoroalkylpentanoyl chloride (CF$_2$ perfluoro homolog distribution as shown in title) was added to a mixture of 19 g of diethyl ether and 2.47 g (24.46 mmol) triethyl amine. After work up, 7.45 g of aldoketene dimer was obtained. Characteristic spectral data: see general procedure.

EXAMPLE 6

Preparation of Fluorinated β-Lactone Aldoketene Dimer With y =4 (<4%),6 (35%), 8 (30%), 10 (17%), 12 (8%),14 or more (<6% and Z=CH=CH(CH$_2$)$_7$: Following the general procedure, 35.0 g of 11-perfluoroalkyl-10-undecenoyl chloride (CF$_2$ perfluoro homolog distribution as shown in title) was added to a mixture of 110 g of 1,2-dichloropropane and 6.25 g triethyl amine. After work up, 28.9 g of aldoketene dimer was obtained. Characteristic data: dark liquid; Characteristic spectral data: see general procedure. See Example 7 for additional characteristic spectra data.

EXAMPLE 7

Preparation of Fluorinated β-Lactone Aldoketene Dimer With y =6 and Z=CH=CH(CH$_2$); Following the general procedure, 73.06 g (140.65 mmol) of 11-perfluorohexyl-10-undecenoyl chloride was added to a mixture of 183 g of 1,2-dichloropropane and 15.66 g (154.72 mmol) triethyl amine. After work up, 63.1 g of aldoketene dimer was obtained. Characteristic data: dark liquid; Characteristic spectral data: see general procedure. Additional characteristic spectra data include: H$^1$ NMR (CDCl$_3$) Olefinic protons next to perfluoroalkyl come at 6.4 and 5.1 ppm as complex multiplets, all allylic protons come between 2-2.5 ppm; C$^{13}$ NMR (CDCl$_3$)(proton decoupled spectra) olefinic carbons next to perfluoroalkyl come at 143.2 and 116.9 ppm.

EXAMPLE 8

Preparation of Fluorinated β-Lactone Aldoketene Dimer With y =6 and Z=CH$_2$CH(I)CH$_2$)$_7$: Following the general procedure, 98.18 g (151.4 mmol) of 11-perfluorohexyl-10-iodo-undecanoyl chloride was added to a mixture of 255 ml of 1,2-dichloropropane and 16.86 g (166.6 mmol) triethyl amine. After work up, 81.5 g of aldoketene dimer was obtained. Characteristic data: dark liquid; Characteristic spectral data: see general procedure. Additional characteristic spectra data for Example 8-11: H$^1$NMR (CDCl$_3$) Proton on iodo substituted carbon comes at 4.3 ppm as a mutiplet; C$^{13}$ NMR (CDCl$_3$) (Proton decoupled) carbon α to perfluoroalkyl moiety comes at 41.7 ppm as a triplet, carbon with iodo substitution comes at 40.3 ppm as a singlet.

EXAMPLE 9

Preparation of Fluorinated β-Lactone Aldoketene Dimer With y =4 (<4%),6 (35%), 8 (30%), 10 (17%), 12 (8%),14 or more (<6%) and Z=CH$_2$CH(I)CH$_2$)$_7$: Following the general procedure, 40.0 g (53.4 mmol) of 11-perfluoroalkyl-10-iodo-undecanoyl chloride (CF$_2$ perfluoro homolog distribution as shown in title) was added to a mixture of 125 g of 1,2-dichloropropane and 5.94 g (58.8 mmol) triethyl amine. After work up, 31.4 g of aldoketene dimer was obtained. Characteristic data: dark viscous liquid; Characteristic spectral data: see general procedure and Example 8.

EXAMPLE 10

Preparation of Fluorinated β-Lactone Aldoketene Dimer With y =10 and Z=CH$_2$CH(I)CH$_2$)$_7$: Following the general procedure, 11.0 g (12.98 mmol) of 11-perfluorodecyl-10-iodo-undecanoyl chloride was added to a mixture of 37 ml of 1,2-dichloropropane and 1.44 g (14.28 mmol) triethyl amine. After work up, 9.13 g of aldoketene dimer was obtained. Characteristic data: mp 65°-70° C.; Characteristic spectral data: see general procedure and Example 8.

EXAMPLE 11

Preparation of Fluorinated β-Lactone Aldoketene Dimer With y =6, 8, 10, 12, 14 (y MW ave.=11.18) and Z=CH$_2$CH(I)CH$_2$)$_7$: Following the general procedure, 460.66 g (507.6 mmol) of 11-perfluoroalkyl-10-iodo-undecanoyl chloride (CF$_2$ perfluoro homolog distribution as shown in title) was added to a mixture of 2 kg of 1,2-dichloropropane and 54.86 g (543.2 mmol) triethyl amine. After work up, 339 g of aldoketene dimer was obtained. Characteristic data: mp 70°-110° C.; Characteristic spectral data: see general procedure and Example 8.

EXAMPLE 12

Preparation of Fluorinated β-Lactone Aldoketene Dimer With y=4, 6, 8, 10, 12, 14 (y MW ave.=9.08) and Z=CH$_2$CH(I)(CH$_2$)$_7$:

Following the general procedure, 430.62 g (533.28 mmol) of 11-perfluoroalkyl-10-iodo-undecanoyl chloride (CF$_2$ perfluoro homolog distribution as shown in title) was added to a mixture of 1.10 kg of 1,2-dichloropropane and 58.28 g (575.94 mmol) triethyl amine. After work up, 361.4 g of aldoketene dimer was obtained. Characteristic spectral data: see general procedure and Example 8.

Table 1 summarizes examples 1-12 of the different R$_f$AKD compositions of matter made having the following formula:

TABLE 1

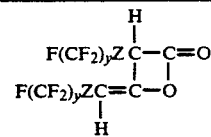

R$_f$AKD MATERIALS MADE

| EXAMPLE # | Y | Z |
|---|---|---|
| 1 | Mixture C | CH$_2$CH(I) (CH$_2$)$_7$ |
| 2 | 4 | (CH$_2$)$_9$ |
| 3 | Mixture A | (CH$_2$)$_9$ |
| 4 | Mixture A | (CH$_2$)$_5$ |
| 5 | Mixture A | (CH$_2$)$_3$ |
| 6 | Mixture A | CH$_2$=CH(CH$_2$)$_7$ |
| 7 | 6 | CH$_2$=CH(CH$_2$)$_7$ |
| 8 | 6 | CH$_2$CH(I) (CH)$_7$ |
| 9 | Mixture A | CH$_2$CH(I) (CH)$_7$ |
| 10 | 10 | CH$_2$CH(I) (CH)$_7$ |
| 11 | Mixture B | CH$_2$CH(I) (CH)$_7$ |
| 12 | Mixture D | CH$_2$CH(I) (CH)$_7$ |

Mixture A: y = 4 (<4%), 6(35%), 8(30%), 10(17%), 12(8%), 14 or more (<6%)
Mixture B: y = 6, 8, 10, 12, 14 (MW ave = 11.18)
Mixture C: y = 4, 6, 8, 10, 12, 14 (MW ave = 8.00)
Mixture D: y = 4, 6, 8, 10, 12, 14 (MW ave = 9.08)

EXAMPLE 13

General procedure for preparing an emulsion/dispersion of florinated aldoketene dimer products: to 4.01 parts (by wt.) of water was added 1.09 parts (dry basis) of a low molecular weight (7 centipoise viscosity at 5% starch in water; Amaizo 2187) tertiary amine derived (0.27% N) starch and 0.19 parts of sodium lignin sulfonate (SLS). The mixture was heated with a steam coil to 95° C. for 30 minutes. The cooked starch was cooled to 25°–30° C. and 0.017 parts of sodium naphthalene sulfonate was added. The starch mixture was then mixed vigorously in a Waring type blender. A solution of 4.65 parts of fluorinated aldoketene dimer and 0–10 parts of organic solvent was added to the starch solution during mixing. The combined mixture was passed through a homogenizer at 3000–4000 psi two times to give a milky white emulsion. The organic solvent was removed from the emulsion under reduced pressure. After cooling to 25° C., the average particle size of the emulsions fell between 0.20 and 0.85 microns. The emulsion remains stable to agglomeration for several weeks. A commercial bacteriostat, such as N-521 ® Biocide made by Stauffer Chemical Company (Westport, CN), is added (0.02–0.06 parts) when the emulsion is to be stored. N.B. Alternatively, the fluorinated aldoketene dimer may be added neat to the warm starch solution followed by homogenization at 7000–8000 psi. The starch solution must be warm enough to melt the particular dimer used prior to homogenization.

The following testing procedures were used:

Surface Sizing Method—A roll of standard kraft paper (SKP) (1:1 Hardwood:Softwood pulp beat to 500 Canadian standard freeness, paper made at pH 6.5, 0.5% Alum, 65 g/m$^2$) was prepared on the Western Michigan University paper machine and used for all testing. Tests were run on paper pretreated with 0.05% size promoter resin S2399.

The following two different surface sizing methods were used.

Organic Solvent Method—Samples of fluorinated aldoketene dimers were dissolved in chloroform or tetrahydrofuran (THF). Paper strips were dipped in the solvent solutions containing the test sizing agents, air dried, wetted with water on a one-nip two-roll press, and drum dried at 104° C. for 20 seconds. The amount of size on the paper was calculated based on the weight of the solvent solution picked up by the paper strip. The sizes were applied to the paper at levels varying from 0.07 to 0.35 weight percent.

Table 3 gives the sizing results from the organic solvent method.

Emulsion/Dispersion Method—Paper strips were passed through a single nip two roll press containing dilutions of the dimer emulsions/dispersions and drum dried at 104° C. for 20 seconds. The amount of size on the paper was calculated based on the weight of the aqueous emulsion/dispersion picked up by the paper strip. The sizes were applied to the paper at levels varying from 0.07 to 0.35 weight percent.

Table 4 gives the sizing results from the emulsion/dispersion method.

Using the tests described below as respectively indicated, testing was run on the treated paper to determine the relative degree of water resistance (HST), the hot water resistance (boiling boat test), the oil resistance (the modified kit test #), and hot oil resistance (hot corn oil float test).

Hercules Size Test (HST)

(To determine the degree of water sizing). The change in reflectance of paper is measured as an aqueous solution of dye penetrates from the other side. The liquid is contained in a ring on top of the paper, and the change in reflectance is measured photoelectrically from the bottom. A convenient end point is chosen, for example, a reduction in reflected light of 20%. The instrument contains a timer that stops automatically when the reflected light falls below the chosen end point. An aqueous solution of naphthol green dye and 1% formic acid were used in the following experiments. As the time increases, the resistance to water penetration increases. Unsized paper will fail after zero seconds, lightly sized paper will register times ranging from 5–20 seconds, moderately sized paper from 21–100, well sized paper from 101–400 seconds, and hard sized paper from 401–2000 seconds.

Boiling Boat Test (BB)

(To determine the degree of hot water sizing). A square boat is formed from the paper sample and floated on the surface of lightly boiling distilled water. The time required to reach an arbitrary end point is recorded (100% penetration over 100% of the paper surface area for this work). As the test time increases, the resistance to hot water penetration increases. Unsized paper would register zero seconds, lightly sized paper gives times ranging from 5–20 seconds, moderately sized paper from 21–100 seconds, well sized paper from 101–600 seconds, and hard sized paper will give greater than 600 seconds. If after 600 seconds, the paper is not 100% saturated, the experiment is stopped and the percent saturation noted.

Modified Kit Test (Kit; Tappi Useful Method 557)

(To determine the degree of oil sizing). Sixteen test solutions consisting of different mixtures of toluene, heptane, and castor oil are premixed. The component ratios are shown in Table 2. Each kit oil is dropped on a sheet of paper placed on a clean flat surface from a height of 2.5 cm above the sheet of paper. After 15 seconds from the completion of dropping of the mixed solvent, conditions of the paper sheet, where the mixed solvent is dropped, is observed. When any dark spot is formed, the oil resistance is evaluated as "unacceptable" irrespective of the area of the spot. When no spot is formed, the oil resistance is evaluated as 'acceptable'. The oil resistance is expressed in terms of the maximum kit solution for which the oil resistance is acceptable. The larger the number of mixed solvent, the better the oil resistance of paper. Unsized paper would give a zero rating, moderate sized paper would give a 1–3 rating, well sized paper would give a 4–8 rating, and hard sized paper would give a 9–16 rating.

TABLE 2

| | Kit Test Solution Mixtures | | |
|---|---|---|---|
| Kit Number | Castor Oil (ml) | Toluene (ml) | Heptane (ml) |
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |
| 13 | 0 | 70 | 130 |
| 14 | 0 | 50 | 150 |
| 15 | 0 | 30 | 170 |
| 16 | 0 | 0 | 200 |

Hot Corn Oil Float Test (HOF)

(To determine the degree of hot oil sizing). A square boat is formed from the paper sample and floated on the surface of 116° C. corn oil. The time required to reach an arbitrary end point is recorded (100% saturation for this work). As the test time increases, the resistance to hot oil penetration increases. Unsized paper would give zero to two seconds of resistance while hard sized paper would give greater than 600 seconds of resistance.

The following tables of data exemplify the sizing efficiency obtained when paper is surface treated with organic solvent solutions (Table 3) or emulsions/dispersions (Table 4) of fluorinated aldoketene dimer. The data show that the $R_fAKD$ materials are unique in that they provide paper with a more efficient "combination" of water, hot water, oil, and hot-oil sizing (HST test, Boiling Boat test, Kit test, and Hot Corn Oil test respectively). This increased efficiency is demonstrated by comparisons with existing commercial products.

Tables 3 and 4 illustrate that the most useful commercial sizing agents do not provide as much sizing efficiency as $R_fAKD$ materials of this invention in all four sizing areas at the same time (water, hot-water, oil, and hot-oil sizing).

The importance of the unsaturated aldoketene $\beta$-lactone dimer structure is illustrated in Table 4. When y=12 and Z=mixture A, no $\beta$-lactone structure was formed and very little sizing is obtained.

The last entry in Table 4 illustrated that the $R_fAKD$ materials are effective on alkaline paper containing no alum.

The following definitions apply for Table 3:
Commercial Size A: Lodyne® P201—CIBA GEIGY Commercial size
Commercial Size B: Scotchban® FC807—3M Commercial size
Commercial Size C: Scotchban® FX810—3M Commercial size
Commercial Size D: Hercon® 70—Hercules Incorporated Commercial size
Mixture A: y=4(<4%),6(35%),8(30%),10(17%), 12(8%),14 or more (<6%)
Mixture B: y=6,8,10,12,14 (MW ave=11.18)
Mixture C: y=4,6,8,10,12,14 (MW ave=8.00)
Mixture D: y=4,6,8,10,12,14 (MW ave=9.08).

All the commercial sizes are sold as aqueous emulsion/dispersions (or aqueous solutions) and were applied to the paper as such.

Testing and application procedures are as described for the organic solvent surface sizing examples.

TABLE 3

SOLVENT SURFACE SIZING RESULTS

| ADD'N LEVEL (wt %) | SIZE USED | 0 Days Aging Dried at 150° C., 10 min | | 7 Day Aged | | 116° C. CORN OIL FLOAT (s) |
|---|---|---|---|---|---|---|
| | | HST (s) | KIT (#) | HST (s) | KIT (#) | B. BOAT (s) |
| 0.07 | Commercial | | | 3 | 5 | 1 | 600 (50%) |
| 0.11 | Size A | | | 16 | 6+ | 3 | |
| 0.15 | | | | 4 | 10 | 14 | 600+ |
| 0.35 | | | | 206 | 16 | 83 | |
| 0.07 | Commercial | | | 4 | 5 | 1 | 600+ |
| 0.11 | Size B | | | 13 | 7 | 4 | |
| 0.15 | | | | 98 | 9 | 5 | |
| 0.35 | | | | 166 | 12 | 24 | |
| 0.07 | Commercial | | | 64 | 1 | 24 | 600 (80%) |
| 0.11 | Size C | | | 117 | 1 | 37 | 600 (10%) |
| 0.15 | | | | 193 | 4 | 101 | 600 (15%) |
| 0.35 | | | | 377 | 5 | 198 | 600+ |
| 0.07 | Commercial | | | 550 | 0 | 600+ | 0 |
| 0.11 | Size D | | | 1200 | 0 | | 0 |
| 0.15 | | | | 2000+ | 0 | | 0 |
| 0.35 | | | | 2000+ | 0 | | 0 |
| 0.07 | Y = Mixture C | 2079 | 5 | 1117 | 4 | 600+ | 600 (5%) |
| 0.11 | Z = $(CH_2)_9$ | 1860 | 5 | 1220 | 5 | | 600+ |
| 0.15 | | 1825 | 6 | 1179 | 5 | | |
| 0.35 | | 1247 | 6 | 1268 | 5 | | |
| 0.07 | Y = Mixture A | 1695 | 5 | 1096 | 5 | 600+ | 600+ |
| 0.11 | Z = $(CH_2)_9$ | 1894 | 7 | 1103 | 5 | | |
| 0.15 | | 1973 | 7 | 1068 | 4 | | |
| 0.35 | | 1798 | 6 | 1080 | 5 | | |
| 0.07 | Y = 4 | | | 931 | 3 | 600+ | 600 (sp) |
| 0.11 | Z = $(CH_2)_9$ | | | 1304 | 3 | 600+ | |
| 0.15 | | | | 1050 | 2 | | |
| 0.07 | Y = 12 | 1 | 0 | 1 | 0 | 0 | 0 |
| 0.11 | Z = $(CH_2)_9$ | 44 | 0 | 5 | 0 | 0 | 0 |
| 0.15 | No $\beta$-lactone | 925 | 0 | 147 | 0 | 0 | 0 |
| 0.07 | Y = Mixture A | | | 1071 | 5 | 600+ | 600+ |
| 0.11 | Z = $(CH_2)_5$ | | | 1469 | 5+ | 600+ | 600+ |
| 0.15 | THF | | | 1491 | 7 | | |
| 0.35 | | | | 1251 | 7+ | | |
| 0.07 | Y = Mixture A | | | 1148 | 3 | 600+ | 600 (55%) |
| 0.11 | Z = $(CH_2)_3$ | | | 1894 | 5 | 600+ | 600+ |
| 0.15 | THF | | | 1581 | 5 | | |
| 0.35 | | | | 1154 | 5 | | |
| 0.07 | Y = Mixture A | 2162 | — | 869 | 2 | 600+ | 30 |
| 0.11 | Z = $CH_2CH(I)(CH_2)_7$ | 1677 | 4 | 1100 | 2 | | 600 (10%) |
| 0.15 | | 2548 | 5 | 1171 | 3 | | 600 (5%) |
| 0.35 | | 1825 | 4 | 1017 | 4 | | 600 (5%) |
| 0.07 | Y = Mixture D | 2060 | 4 | 931 | 3 | 600+ | 600 (5%) |
| 0.11 | Z = $CH_2CH(I)(CH_2)_7$ | 1961 | 5 | 1164 | 3 | | 600+ |
| 0.15 | | 2017 | 6 | 1226 | 4 | | |

TABLE 3-continued

SOLVENT SURFACE SIZING RESULTS

| ADD'N LEVEL (wt %) | SIZE USED | 0 Days Aging Dried at 150° C., 10 min HST (s) | KIT (#) | 7 Day Aged HST (s) | KIT (#) | B. BOAT (s) | 116° C. CORN OIL FLOAT (s) |
|---|---|---|---|---|---|---|---|
| 0.35 |  | 1849 | 6 | 1201 | 4 |  |  |
| 0.07 | Y = 10 | 1129 | 5 | 1221 | 4 | 600+ | 600 (50%) |
| 0.11 | Z = $CH_2CH(I)(CH_2)_7$ | 1646 | 6 | 1131 | 4 | * | 600 (10%) |
| 0.15 |  | 1542 | 7 | 1427 | 5 |  | 600+ |
| 0.35 |  | 1641 | 8 | 1423 | 7 |  |  |
| 0.07 | Y = Mixture B |  | 2 | 556 | 2 | 19 | 4 |
| 0.11 | Z = $CH_2CH(I)(CH_2)_7$ |  | 4 | 685 | 3 | 600 (90%) | 9 |
| 0.15 |  |  | 4 | 750 | 3 | 600 (35%) | 600 (80%) |
| 0.35 |  |  | 5 | 1027 | 5 | 600+ | 600 (20%) |
| 0.07 | Y = Mixture A | 1461 | 5 | 908 | 4 | 600+ | 600+ |
| 0.11 | Z = $CH_2CH(I)(CH_2)_7$ | 1386 | 6 | 1207 | 4 |  |  |
| 0.15 |  | 1331 | 5 | 949 | 5 |  |  |
| 0.35 |  | 1262 | 4 | 1047 | 3 |  |  |
| 0.07 | Y = 6 | 1554 | 4 | 1233 | 3 | 600+ | 600 (20%) |
| 0.11 | Z = $CH_2CH(I)(CH_2)_7$ | 1434 | 4 | 1183 | 4 |  | 600+ |
| 0.15 |  | 1363 | 4 | 1154 | 4 |  |  |
| 0.35 |  | 1349 | 2 | 1146 | 2 |  |  |
| 0.07 | Y = Mixture A |  |  | 1227 | 2+ | 600+ (60%) |  |
| 0.11 | Z = $CH=CH(CH_2)_7$ |  |  | 1335 | 4 | 600+ (95%) |  |
| 0.15 | THF |  |  | 1246 | 5 | 600+ |  |
| 0.35 |  |  |  | 1502 | 4 |  |  |
| 0.07 | Y = 6 | 566 | 4 | 1281 | 4 | 600+ | 600+ |
| 0.11 | Z = $CH=CH(CH_2)_7$ | 1913 | 4 | 698 | 3 |  |  |
| 0.15 |  | 1569 | 5 | 1300 | 1 |  |  |
| 0.35 |  | 1777 | 1 | 1320 | 0 |  |  |

The following definitions apply for Table 4:
Commercial Size A: Lodyne ® P201 - CIBA GEIGY Commercial size
Commercial Size B: Scotchban ® FC807 - 3M Commercial size
Commercial Size C: Scotchban ® FX810 - 3M Commercial size
Commercial Size D: Hercon ® 70 - Hercules Incorporated Commercial size.
Mixture A: y = 4 (<4%), 6 (35%), 8 (30%), 10 (17%), 12 (8%), 14 or more (<6%)
Mixture B: y = 6, 8, 10, 12, 14, (MW ave = 11.18)
Mixture C: y = 4, 6, 8, 10, 12, 14 (MW ave = 8.00)
Mixture D: y = 4, 6, 8, 10, 12, 14 (MW ave = 9.08).

Testing and application procedures are described for the emulsion/dispersion surface sizing examples.

TABLE 4

EMUSLSION/DISPERSION SURFACE SIZING

| ADDN'N (wt %) | SIZE USED | 0 Days Aging Cured at 150° C., 10 min. HST (s) | KIT (#) | 7 Day Aged HST (s) | KIT (#) | B. BOAT (s) | 116° C. CORN OIL FLOAT (s) |
|---|---|---|---|---|---|---|---|
| 0.07 | Commercial |  |  | 3 | 5 | 1 | 600 (50%) |
| 0.11 | Size A |  |  | 16 | 6+ | 3 |  |
| 0.15 |  |  |  | 4 | 10 | 14 | 600+ |
| 0.35 |  |  |  | 206 | 16 | 83 |  |
| 0.07 | Commercial |  |  | 4 | 5 | 1 | 600+ |
| 0.11 | Size B |  |  | 13 | 7 | 4 |  |
| 0.15 |  |  |  | 98 | 9 | 5 |  |
| 0.35 |  |  |  | 166 | 12 | 24 |  |
| 0.07 | Commercial |  |  | 64 | 1 | 24 | 600 (80%) |
| 0.11 | Size C |  |  | 117 | 1 | 37 | 600 (10%) |
| 0.15 |  |  |  | 193 | 4 | 101 | 600 (15%) |
| 0.35 |  |  |  | 377 | 5 | 198 | 600+ |
| 0.07 | Commercial |  |  | 550 | 0 | 600+ | 0 |
| 0.11 | Size D |  |  | 1200 | 0 |  | 0 |
| 0.15 |  |  |  | 2000+ | 0 |  | 0 |
| 0.35 |  |  |  | 2000+ | 0 |  | 0 |
| 0.07 | Y = Mixture A | 1299 | 1 | 596 | 0 | 600+ | 43 |
| 0.11 | Z = $(CH_2)_9$ | 1232 | 4 | 784 | 3 |  | 600 (sp) |
| 0.15 |  | 1380 | 5 | 969 | 5 |  | 600+ |
| 0.35 |  | 1703 | 6 | 1369 | 6 |  |  |
| 0.07 | Y = 4 |  |  | 497 | 0 | 600+ | 0 |
| 0.11 | Z = $(CH_2)_9$ |  |  | 1190 | 1 |  | 7 |
| 0.15 |  |  |  | 998 | 3 |  | 600 (sp) |
| 0.35 |  |  |  | 844 | 3 |  | 600+ |
| 0.07 | Y = Mixture A |  |  | 748 | 4 | 600+ | 600+ |
| 0.11 | Z = $(CH_2)_5$ |  |  | 1018 | 5 |  |  |
| 0.15 |  |  |  | 1055 | 6 |  |  |
| 0.35 |  |  |  | 1179 | 6 |  |  |
| 0.07 | Y = 10 | 971 | 0 | 686 | 0 | 600+ | 61 |
| 0.11 | Z = $CH_2CH(I)(CH_2)_7$ | 1259 | 4 | 683 | 4 |  | 600+ |
| 0.15 |  | 1476 | 5 | 1205 | 5 |  |  |
| 0.35 |  | 1982 | 8 | 1286 | 8 |  |  |
| 0.07 | Y = Mixture A | 812 | 0 | 540 | 0 | 600+ | 600 (95%) |

TABLE 4-continued

EMUSLSION/DISPERSION SURFACE SIZING

| ADDN'N (wt %) | SIZE USED | 0 Days Aging Cured at 150° C., 10 min. HST (s) | KIT (#) | HST (s) | 7 Day Aged KIT (#) | B. BOAT (s) | 116° C. CORN OIL FLOAT (s) |
|---|---|---|---|---|---|---|---|
| 0.11 | Z = CH$_2$CH(I)(CH$_2$)$_7$ | 1053 | 4 | 730 | 3 | | 600 (5%) |
| 0.15 | | 1230 | 5 | 879 | 4 | | 600+ |
| 0.35 | | 1473 | 5 | 1145 | 5 | | |
| 0.07 | Y = Mixture A | 760 | 0 | | | | |
| 0.11 | Z = CH$_2$CH(I)(CH$_2$)$_7$ | 1289 | 3 | | | | |
| 0.15 | 22 day old | 1255 | 4 | | | | |
| 0.35 | emulsion | 1586 | 5 | | | | |
| 0.07 | Y = 6 | 765 | 0 | 553 | 0 | 600+ | 3 |
| 0.11 | Z = CH$_2$CH(I)(CH$_2$)$_7$ | 1071 | 4 | 676 | 2 | | 600 (10%) |
| 0.15 | | 1414 | 4 | 1166 | 3 | | 600 (sp) |
| 0.35 | | 1332 | 4 | 1205 | 4 | 600+ | |
| 0.07 | Y = Mixture A | | | 447 | 0 | 600+ | 2 |
| 0.11 | Z = CH=CH(CH$_2$)$_7$ | | | 921 | 3 | 600+ | |
| 0.15 | | | | 866 | 3 | | |
| 0.35 | | | | 924 | 4 | | |
| 0.07 | Y = 6 | 1252 | 3 | 784 | 1 | 600+ | 600 (80%) |
| 0.11 | Z = CH=CH(CH$_2$)$_7$ | 1148 | 4 | 1007 | 4 | | 600+ |
| 0.15 | | 1368 | 5 | 846 | 4 | | |
| 0.35 | | 1414 | 4 | 993 | 1 | | |
| 0.07 | Y = Mixture A | 1076 | 0 | 651 | 0 | 600+ | 3 |
| 0.11 | Z = CH=CH(CH$_2$)$_7$ | 816 | 3 | 848 | 3 | | 600 (sp) |
| 0.15 | 29 day old | 1195 | 5 | 960 | 2 | | 600+ |
| 0.35 | emulsion | 1403 | 4 | 992 | 1 | | |
| 0.07 | Y = Mixture A | 597 | 0 | 361 | 0 | 600+ | 2 |
| 0.11 | Z = (CH$_2$)$_9$ | 1028 | 3 | 605 | 3 | | 600 (sp) |
| 0.15 | ph 7.9 | 1227 | 4 | 817 | 4 | | 600+ |
| 0.35 | no Alum in Paper | 1478 | 6 | 1333 | 6 | | |

Internal Addition Tests

R$_f$AKD emulsion/dispersions were added to the pulp fiber during production of molded fiber articles. Recycled newspapers were used as fiber furnish and the articles were molded at a pH of 7.5. The articles were formed on a pilot scale (Table 5) molded fiber paper machine and dried in a convection oven at 135°-162° C. to a moisture content of 0-18% by weight, preferably 2-8% by weight.

After drying, the molded articles were tested for hot-water and hot oil sizing.

Hot Water Test: Distilled water at 95°-100° C. is poured onto a molded fiber article. After 15 minutes the water was poured off and the article was examined for surface wetting and penetration by the water. The less surface wetting and penetration the better the water sizing.

Hot Oil Test: Corn oil at 83°-95° C. was poured onto a molded fiber article. After 15 minutes the article was examined for surface wetting and penetration by the oil. The less surface wetting and penetration the better the oil sizing.

Oil Pickup: Equal portions of 83°-95° C. corn oil were poured onto preweighed molded fiber articles of equal moisture content and allowed to stand for 15 minutes. The oil was gravity drained from the articles for 45 minutes and any excess oil remaining on the articles is removed with a clean cloth or towel. The weight of the oil picked up by the article was then determined. The lower the weight of oil pickup the better the oil sizing.

The test results shown in Table 5 show that the R$_f$AKD emulsion/dispersions provide more efficient hot water and hot oil sizing than commercial sizing systems that employ two separate sizing materials: one for water and one for oil sizing.

Definitions used in Table 5:

CC—Contact Cure—Dried between two hot metal molds (Upper—182° C.; Lower 171° C.).
OC—Oven Cure (177° C. or 149° C.); oven dried.
F—Fail
P—Pass
G—Good
E—Excellent
B—Bad
VB—Very Bad
SW—Surface Wetted
PN—Penetration
SL—Slight
S—Slow
SP—Spotty
RB—Rib Area
NK—Neck Area
DK—Dark
P201—Ciba Geigy Lodyne® P201 (Oil Sizing Agent)
H76—Hercon® 76
ASA—Nalco 7540 (Alkenyl Succinic Anhydride Water Sizing Agent & Size Retention Aid).
7541—Nalco Cationic Emulsification Polymer
Alk—Alkalinity as ppm sodium bicarbonate
S2399—Hercules resin S—2399 used for retention
D711—Hercules polyamine resin Kymene® 367 used for chemical retention
R$_f$AKD#—Refer to Example # in Table 1.

TABLE 5

| | $R_fAKD$ Internal Sizing In Molded Articles[a] | | | | |
|---|---|---|---|---|---|
| | (% wt/wt) | | Sizing 0 Days Aging | | |
| Run # | Internal Additives | Drying[b] Conditions | Hot Water | Hot Oil | Other |
| 1 | 0.3625% P201<br>0.4875% ASA<br>0.4875% 7541<br>150 ppm Alk | 18 min. | P PN NK | VB SW | Pulp<br>pH = 7.5 |
| 2 | 0.3625% $R_fAKD$ 12<br>0.3625% S2399<br>150 ppm Alk | 28 min. | P E | P E | pH = 7.5 |
| 3 | 0.375% $R_fAKD$ 12<br>0.3625% S2399<br>150 ppm Alk | 25 min. | P E | P E | pH = 7.5<br>pH = 7.5 |
| 4 | 0.375% $R_fAKD$ 1<br>0.3625% S2399<br>150 ppm Alk | 25 min. | P E | P VG | pH = 7.5 |
| 5 | 0.3625% $R_fAKD$ 3<br>0.3625% S2399<br>150 ppm Alk | 20 min. | PE | P E | pH = 7.5 |
| 6 | 0.375% P201<br>0.4875% ASA<br>0.4875% 7541 | 20 min. | P E | F PN | pH = 6.2 |
| 7 | 0.375% $R_fAKD$ 12<br>0.3625% S2399 | 23 min. | P E | P G | pH = 6.2 |

[a]Pulp furnish - Recycled Newsblank.
Additives were added as a percentage of dry cellulose weight.
Additives were added to the pulp slurry before molded articles were formed.
Molded articles were made on a pilot scale molded article paper machine.
[b]Runs 1-5: Molded articles were oven dried at 177° C.
Runs 6 & 7: Molded articles were oven dried at 149° C.

I claim:

1. An aldoketene dimer having the structure:

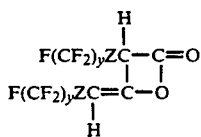

in which y=1-18, Z=$(CH_2)_n$,

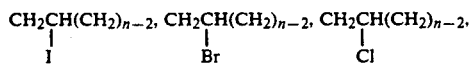

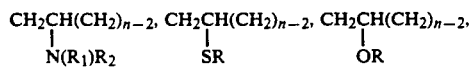

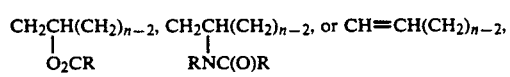

in which R, $R_1$ and $R_2$ are any alkyl radical, and n is an integer from 3 to 18 inclusive.

2. An aldoketene dimer having the structure:

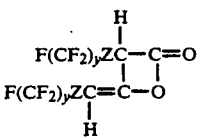

in which y=1-18, $Z = (CH_2)_n$, 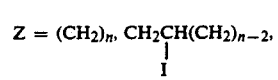

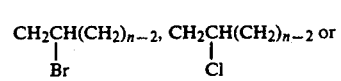

or CH=CH$(CH_2)_{n-2}$, and n is an integer from 3-18 inclusive.

* * * * *